United States Patent [19]

Trznadel

[11] Patent Number: 4,693,241
[45] Date of Patent: Sep. 15, 1987

[54] ELASTIC BANDAGE KNEE SUPPORT
[76] Inventor: Amalia Trznadel, 32 St. Kolby Dr., Holyoke, Mass. 01040
[21] Appl. No.: 887,446
[22] Filed: Jul. 21, 1986
[51] Int. Cl.⁴ .......................................... A61F 13/00
[52] U.S. Cl. ................................................ 128/157
[58] Field of Search ................ 128/157, 80 R, 166, 128/166.5

[56] References Cited
U.S. PATENT DOCUMENTS 3,463,147 8/1969 Stubbs ............................. 128/80 R
3,926,186 12/1975 Nirschl ............................ 128/80 R
3,945,046 3/1976 Strumgren ...................... 128/80 C
4,370,978 2/1983 Palumbo ......................... 128/80 C Primary Examiner—Gregory E. McNeill
Attorney, Agent, or Firm—Ross, Ross & Flavin

[57] ABSTRACT

An elasticized leg encircling bandage knee support having incorporated therewith a semi-resilient pad releasably and adjustably affixed thereto, the bandage and the pad being adapted to be used in various positions or orientation for bearing against selected portions of the knee joint to give desired support thereto and to relieve pain.

6 Claims, 8 Drawing Figures

ELASTIC BANDAGE KNEE SUPPORT

BACKGROUND OF THE INVENTION

1. FIELD OF THE INVENTION

The invention relates to bandages and more particularly to bandages employable as knee supports.

2. DESCRIPTION OF RELATED ART

A wide variety of knee bandages and supports is shown in the prior art. However, most are cumbersome, or expensive, or difficult to apply to the knee, or uncomfortable to wear, or fail to stay in place after being applied, or fail to relieve pain.

SUMMARY OF THE INVENTION

The invention teaches an elasticized leg encircling bandage having incorporated therewith a semi-resilient pad releasably and adjustably affixed thereto, the bandage and the pad being adapted to be used in various positions of orientation for bearing against selected portions of the knee joint to give desired support thereto and to relieve pain.

The bandage and knee support hereof is lightweight, inexpensive, easy to apply to the knee, comfortable to wear, stays firmly in place once applied, and is effective to relieve pain.

It also gives desired support and comfort to different portions of the knee, depending upon its orientation when applied to the knee.

DESCRIPTION OF THE PREFERRED EMBODIMENT

Figure 1:
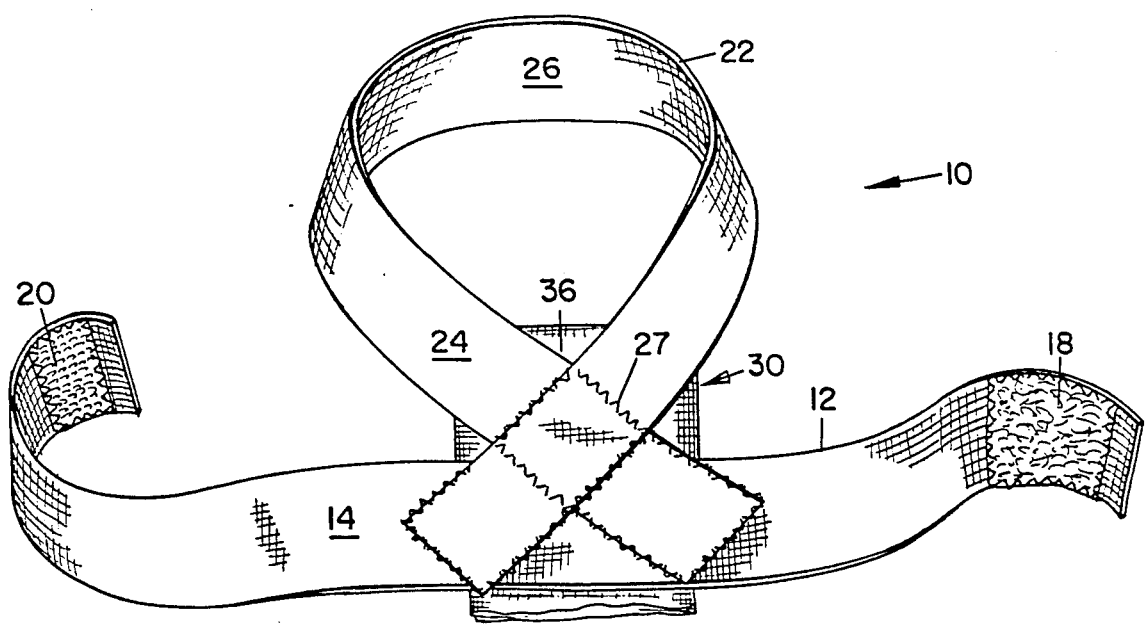
FIG. 1 is a top plan view of the elastic bandage knee support of the invention.
Figure 2:
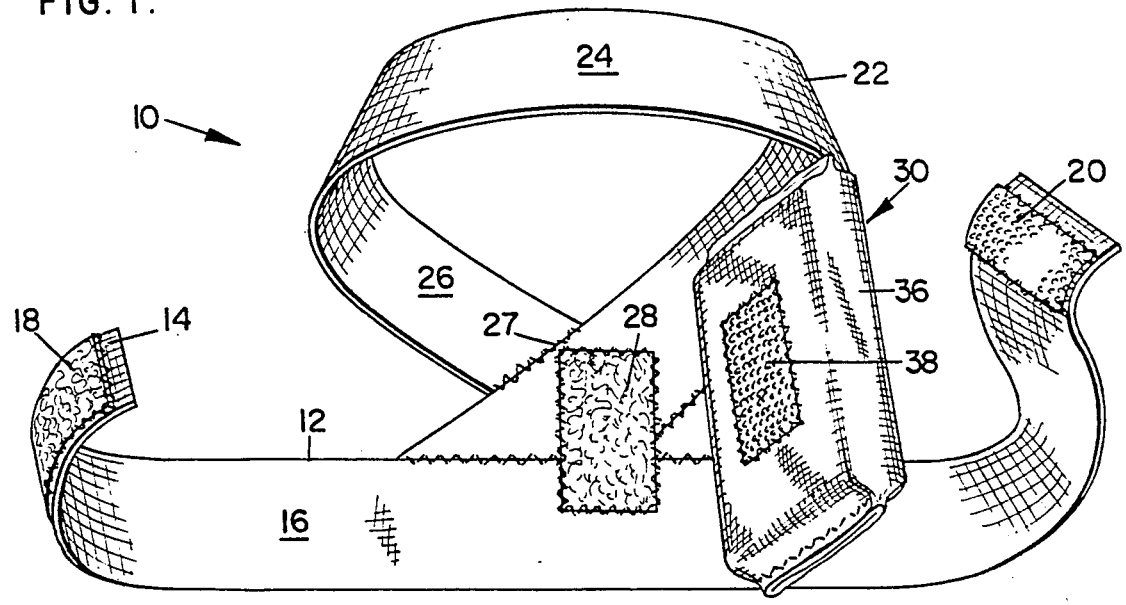
FIG. 2 is an inverted, exploded plan view thereof.

The elastic bandage knee support is generally indicated by 10 and includes a first horizontally disposed elasticized strap 12 having front and rear planar faces 14 and 16 respectively. Strap 12 has a rectangular felt or other fabric patch 18 fixed to front face 14 adjacent one end thereof, and a rectangular Velcro patch 20 fixed to rear face 16 adjacent the opposite end thereof.

Velcro patch 20 is adapted to mate and interlock with fabric patch 18 when one end of elastic strap 12 is brought into overlapping position relative to the other end.

A second elasticized strap 22 having front and rear planar faces 24 and 26 respectively is formed in the shape of a loop with its ends criss-crossing and being stitched together as by stitching 27 to form an "X," with the ends of the strap being fixed to the front face 14 of first elastic strap 12 centrally of the latter so as to extend vertically upwardly therefrom.

A vertically oriented rectangular felt or other fabric patch 28 is fixed to the rear face 26 of second elastic strap 22 at the intersection of the crossed strap ends and is also fixed to the rear face 16 of first elastic strap 12.

A pad, generally indicated by 30, preferably includes a semi-resilient core 32 of rubber or plastic or similar material fixed to a rigid or semi-rigid backing member 34, with the whole being encased in a wrapper 36 of a soft fabric material and preferentially, although not obligatorily, presenting a somewhat rectangular shape in plan.

A rectangular Velcro patch 38 is fixed to the rear planar face of pad 30 and is adapted to engage and interlock with fabric patch 28 on elastic straps 12 and 22 when the pad is positioned thereagainst.

Figure 3:
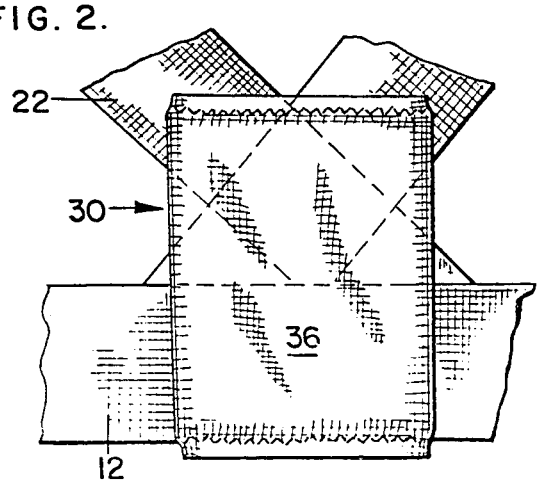
FIGS. 3 and 4 are fragmentary inverted plan views showing the pad of the elastic bandage knee support attached thereto in different positions of orientation.
Figure 4:
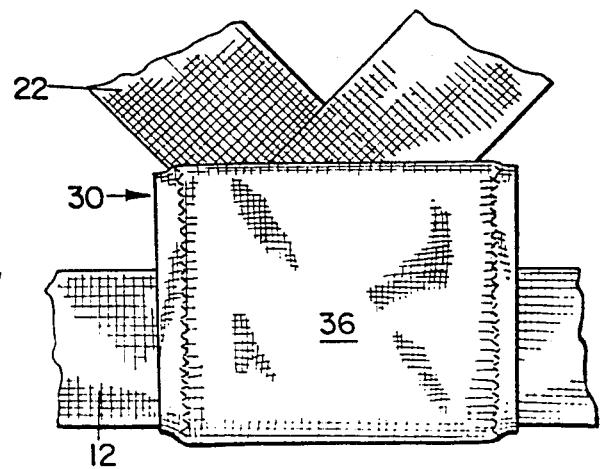

Pad 30 may be disposed in a vertical orientation relative to first elastic strap 12, as shown in FIG. 3, or it may be disposed in a horizontal orientation relative to first elastic strap 12, as shown in FIG. 4, depending upon the particular area of the knee being treated.

For example, in the vertical orientation of FIG. 3, the pad will exert a firm, but gentle bearing pressure against the kneecap and the anterior and posterior cruciate ligaments.

In the horizontal orientation of FIG. 4, the pad will exert a firm, but gentle bearing pressure against the kneecap, tibia and fibula.

Figure 5:
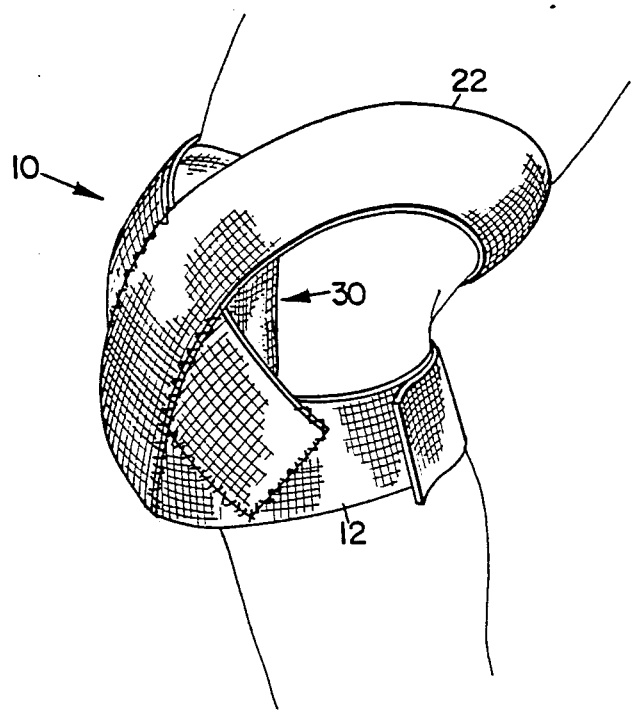
FIGS. 5 and 6 are perspective views showing the elastic bandage knee support as worn at the knee in different positions of orientation.
Figures 6, 7:
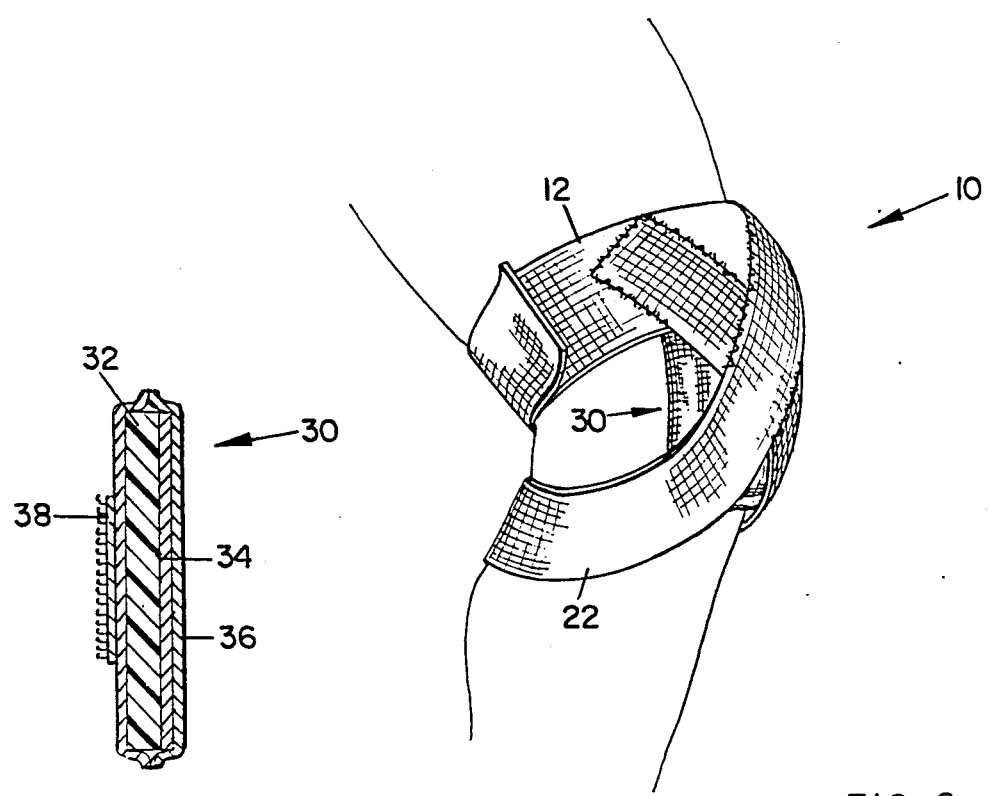
FIG. 7 is a cross-sectional view of the pad.
Figure 8:
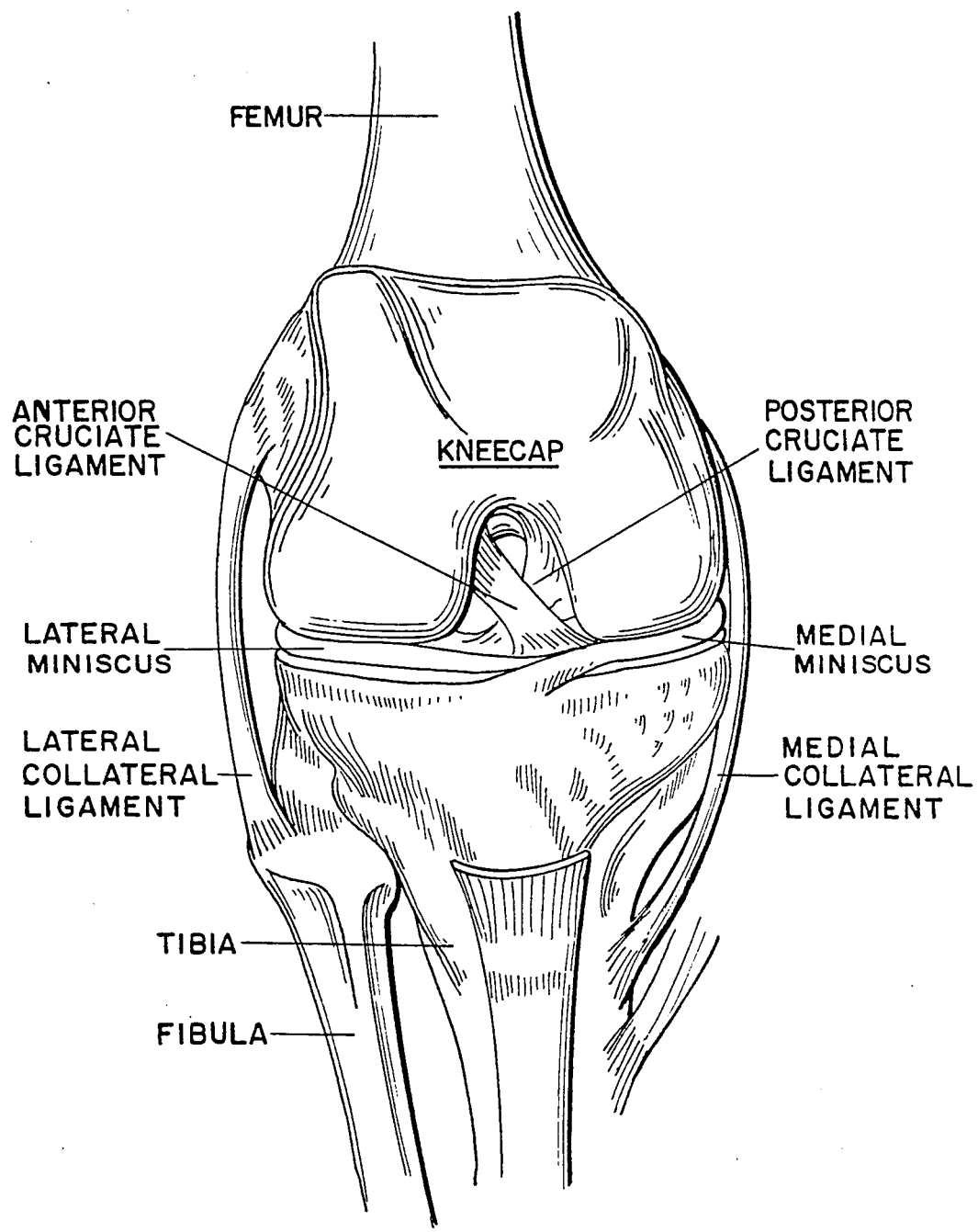
FIG. 8 is an elevational detail view of the human knee.

The elastic bandage and knee support may be worn on the leg in the orientations of either FIGS. 5 or 6.

In the FIG. 5 orientation, the loop formed by second elastic strap 22 is disposed above the knee joint, in encircling manner about the leg, while the first elastic strap 12 is disposed below the knee joint in encircling manner about the leg with the ends of the strap connected by the interengagement of Velcro patch 20 with fabric patch 18.

In such orientation, pad 30 will exert a firm but gentle bearing pressure against the kneecap, the anterior and posterior cruciate ligaments, and the lateral and medial miniscus.

In the FIG. 6 orientation, the loop formed by second elastic strap 22 is disposed below the knee joint, in encircling manner about the leg, while the first elastic strap 12 is disposed above the knee joint in encircling manner about the leg with the ends of the strap connected by the interengagement of Velcro patch 20 with fabric patch 18.

In such orientation, pad 30 will exert a firm but gentle bearing pressure against the kneecap and against the lateral and medial miniscus and the tibia.

The elastic bandage and knee support may also be worn so that pad 30 is disposed at either side of the knee joint, so as to bear against either the medial collateral ligament and tibia on one side, or the lateral collateral ligament, tibia and fibula on the other side.

The strap and loop and pad arrangement allows secure but easy positioning of the bandage and knee support on the leg in virtually limitless positions of orientation at the knee joint.

I claim:

1. An elasticized leg encircling bandage knee support for placement at the knee joint of a wearer comprising:

a first elasticized horizontally-disposed strap having opposite free ends;

a second elasticized strap formed in a loop and having crossed ends fixed centrally of the first strap, the loop being disposed vertically relative to the first strap and adapted to encircle the leg of a wearer;

releasable fastening means on the free ends of the first strap permitting releasable interengagement of the free ends with each other when the strap encircles the leg of a wearer;

a semi-resilient pad releasably and adjustably fixed to the first and second straps in any selected pressure-exerting position of orientation.

2. An elasticized leg encircling bandage knee support according to claim 1, wherein the first strap is disposed above the knee joint of a wearer and the second strap is disposed below the knee joint of a wearer.

3. An elasticized leg encircling bandage knee support according to claim 1, wherein the first strap is disposed below the knee joint of a wearer and the second strap is disposed above the knee joint of a wearer.

4. An elasticized leg encircling bandage knee support according to claim 1, wherein the pad is disposed in a vertical orientation relative to the first strap and bears against the front of the knee joint.

5. An elasticized leg encircling bandage knee support according to claim 1, wherein the pad is disposed in a horizontal orientation relative to the first strap and bears against the front of the knee joint.

6. An elasticized leg encircling bandage knee support according to claim 1, wherein the pad bears against the side of the knee joint.

* * * * *